United States Patent [19]

Karasawa et al.

[11] 4,307,195

[45] Dec. 22, 1981

[54] IMMOBILIZED ENZYME MEMBRANE

[75] Inventors: Yoshiharu Karasawa; Hisashi Kohkame, both of Hitachi, Japan

[73] Assignee: Hitachi, Ltd., Tokyo, Japan

[21] Appl. No.: 80,026

[22] Filed: Sep. 28, 1979

[30] Foreign Application Priority Data

Sep. 29, 1978 [JP]  Japan .................................. 53-119256

[51] Int. Cl.³ .................... C12M 1/40; C12N 11/04
[52] U.S. Cl. .................................. 435/288; 204/1 T; 435/179; 435/181; 435/182
[58] Field of Search ............... 435/174, 180, 181, 177, 435/182, 179, 288; 210/22; 204/1 T

[56] References Cited

U.S. PATENT DOCUMENTS

| | | | |
|---|---|---|---|
| 3,539,455 | 11/1970 | Clark, Jr. .......................... | 204/1 T |
| 3,542,662 | 11/1970 | Hicks et al. ..................... | 435/288 X |
| 3,705,084 | 12/1972 | Reynolds ........................... | 435/180 |
| 4,033,822 | 7/1977 | Gregor ............................... | 435/179 |

OTHER PUBLICATIONS

Zaborsky, O., Immobilized Ensymes, CRC Press, Cleveland, Ohio, 1973 (pp. 70-74, 103-115 & 127-133).

Selegny, et al., Enzymatically Active Model-Membranes, Physiol. Veg., vol. 9 No. 1, 1971 (pp. 25-30).

Primary Examiner—David M. Naff
Attorney, Agent, or Firm—Craig and Antonelli

[57] ABSTRACT

An immobilized enzyme membrane for use at the working face of an electrochemical electrode is prepared which comprises an asymmetrical membrane integrally formed from a skin layer substantially incapable of permeating an enzyme therethrough but capable of permeating a gas and a liquid, and a sponge layer having pores containing an enzyme immobilized therein by crosslinking and which pores intercommunicate with one another throughout the sponge layer and provide sufficient porosity for retaining a necessary amount of the enzyme. The immobilized enzyme membrane contains a large amount of enzyme, has good diffusion and permeability, and has stabilized enzyme activity for a prolonged period of time. Additionally, there is obtained a quick response time and good analytical precision when the immobilized enzyme membrane is used at the working face of an electrode of electrochemical measuring instruments.

7 Claims, 3 Drawing Figures

IMMOBILIZED ENZYME MEMBRANE

BACKGROUND OF THE INVENTION

This invention relates to an immobilized enzyme membrane, a process for preparing the membrane, and an enzyme electrode apparatus for electrochemically measuring instruments using the immobilized enzyme membrane.

Heretofore, various analytical methods using an immobilized enzyme membrane have been proposed for quantitatively analyzing medically important substances in living bodies, for example, sacharides, urea, chloesterol, or other substances contained in very small amounts in the living body liquids with a good selectivity. These methods provide effective means for detecting components contained in very small amounts in a multi-component liquid by utilizing a substrate peculiarity and a high catalytic activity possessed by the enzyme. However, these methods still have a problem in immobilizing the enzyme and have not been yet widely practically utilized.

The enzyme has been so far immobilized in a membrane state or a membrane according to any of the following methods: (1) a method of enclosing the enzyme with a polyacrylamide gel [Nature 214 986 (1967)], (2) a method of mixing the enzyme with an inert protein such as albumin, etc. as a reinforcing agent, and cross-linking the inert protein by a cross-linking agent [Biotechnology and Bioengineering 15 359 (1973)], (3) a method of absorbing the enzyme in filter paper or cellophane, and cross-linking it by glutaraldehyde [Biotechnology and Bioengineering 15 359 (1973)], (4) a method of ionically bonding the enzyme with an ion-exchange cellulose [Biotechnology and Bioengineering 13 (1971)], (5) a method of adding the enzyme to a collagen fiber solution, placing the solution in an electrolysis cell, passing an electric current through the cell, and electro-depositing a collagen film enclosing the enzyme onto an electrode [Biochemistry, Biophysics Research Communication 47 51 (1972)], (6) a method of physico-chemically immobilizing the enzyme on a porous, organopolymeric film (Japanese Laid-open Patent Application Specification No. 17,889/77), (7) a method of sandwiching an enzyme gel in between two films (Japanese Laid-open Patent Application Specification No. 55,691/77), etc.

A large amount of enzyme can be immobilized according to said method (1), but the strength of a membrane is not enough, and diffusion of substrates and products is poor. According to said method (2), an enzyme load can be increased, but the strength is not sufficient, and a resistance to microorganisms is not sufficient because the protein is used as the reinforcing agent. Said method (3) can be easily carried out, but the enzyme load is not sufficient, and when a film is made thicker to increase the strength, diffusion of substrate, etc. becomes poor; whereas when the film is made thinner, the strength becomes poor. Both methods (4) and (5) can be easily carried out, but a bonding of the enzyme to a carrier is weak, and the enzyme is easily released from the carrier. Said method (6) is to overcome the foregoing drawbacks, but the membrane is perforated from the face side to the back side of the membrane, and thus a sufficient amount of the enzyme cannot be retained in the perforations of the porous membrane. Furthermore, the membrane has not a sufficient porosity and thus the enzyme load is not sufficient. Said method (7) is complicated in its preparation, because the enzyme gel is sandwiched in between two thin films, and increases the production cost, though its enzyme load is large.

SUMMARY OF THE INVENTION

An object of the present invention is to provide an immobilized enzyme membrane having a large enzyme load, a good diffusion permeability for specific materials and a stabilized activity for a prolonged period of time.

Another object of the present invention is to provide an enzyme electrode apparatus for electrochemically measuring instruments with said distinguished characteristics, a good response characteristic, and a good analytical precision.

The present invention provides an immobilized enzyme membrane, which comprises an asymmetical membrane integrally formed from a dense skin layer substantially incapable of permeating an enzyme therethrough but capable of permeating a gas and a liquid therethrough (which will be hereinafter referred to as "skin layer") and a sponge layer having a sufficient porosity for supporting the necessary amount of the enzyme and pores intercommunicated with one another throughout the sponge layer, (which will be hereinafter referred to as "sponge layer"), the enzyme being immobilized in the pores by cross-linking.

The present invention will be described in detail below, referring to the accompanying drawings.

BRIEF DESCRIPTION OF THE DRAWINGS

In FIG. 1, the present immobilized enzyme membrane is schematically given, where numeral 1 is a dense skin layer substantially incapable of permeating enzyme, but capable of permeating a gas and a liquid, and 2 is a sponge layer having a sufficient porosity for retaining the necessary amount of enzyme and pores intercommunicating with one another throughout the sponge layer, the skin layer 1 and the sponge layer 2 are integrally formed, preferably, from the same material, into an asymmetrical immobilized enzyme membrane 3. Therefore, the skin layer 1 and the sponge layer 2 are not formed by bonding the former layer to the latter layer, even though these two layers are formed from the same material.

Figure 1:
FIG. 1 is a cross-sectional view of an immobilized enzyme membrane according to the present invention.

The asymmetrical membrane of the present invention is well known, for example, as the reverse osmosis membrane, and its process and structure are well known, for example, from the following literatures.

(a) S. Manjikian, S. Loeb and J. W. McCutchan: Proc. 1st Int. Symp. on Water desalination, Washington, D. C. (1965), and (b) G. T. Gittens, P. A. Hitchcock, D. C. Sammon and G. E. Wakley: Desalination 8 369 (1970).

In the present invention, the skin layer has a property to permeate low molecular weight substances (including ionic substances) which have been increased or decreased by an enzyme reaction and are to be detected.

Any kind of materials, so far as they can form the so-called reverse osmosis membrane, can be used as the material for the asymmetrical membrane of the present invention. Examples of these materials are cellulose derivatives such as acetyl cellulose, ethyl cellulose, propionyl cellulose, butyryl cellulose, etc., aliphatic and aromatic polyamides, polyamide-imide, polybenzoimidazole, acrylonitrile copolymers, polycarbonate, polyester, polyamino acid, etc. Particularly desirable are cellulose derivatives and polyamino acid, which have an affinity toward the enzyme.

Thickness of the asymmetrical membrane is desirably about 1–about 1,000 $\mu$m, and preferably 30–300 $\mu$m. Thickness of the skin layer in the asymmetrical membrane is desirably about 0.01–about 10 $\mu$m, preferably 0.1–3 $\mu$m. The skin layer has no pores large enough to permeate at least enzyme molecules, whereas the pores formed in the sponge layer consist of pores of various sizes. That is, the pores locating more distant from the skin layer become larger, and the pores at the surface of the sponge layer have pore sizes of about 100–about 500 nm, so that an enzyme solution can freely enter the sponge layer into the pores from said large pore openings. Porosity of the sponge layer of the asymmetrical membrane can be changed to some degree, depending upon membrane-casting conditions, but usually a porosity of about 50–about 90% is appropriate.

The enzyme can be introduced and retained in the pores of the sponge layer according to the ordinary immersion method. More preferably, the introduction and retaining of the enzyme can be carried out easily and efficiently according to a pressure filtration method. That is, according to the present invention, an enzyme solution can be pressure driven into the sponge layer side of the asymmetrical membrane by utilizing the property of reverse osmosis membrane, thereby retaining the enzyme solution in the pores (porous parts) of the sponge layer. At that time, the enzyme does not substantially permeate through the skin layer, and is stably retained in the pores of the sponge layer. The pressure filtration is carried out by pressure driving an aqueous enzyme solution or an aqueous enzyme solution containing a stabilizer from the sponge layer side of the asymmetrical membrane, and can be carried out only by the asymmetrical membrane as used in the present invention. In the case of the ordinary mere porous membrane such as fibrous materials, for example, paper, pores are penetrated therethrough from one end of the membrane to another, and there is usually no distinction between the face side and the back side of the membrane, that is, the face side and the back side are in quite identical states, and thus the enzyme solution cannot be pressure driven and retained therein by the filtration.

The aqueous enzyme solution to be introduced can have any desired enzyme concentration, but about 0.1–about 50 mg/ml is generally desirable. The pressure for pressure driving is superatmospheric, and can be freely selected, so long as the asymmetrical membrane cannot undergo compaction or damaging, but it is desirably 0.2–1 MPa.

Filtration time depends upon the enzyme concentration of enzyme solution, but is usually within a range of 5 minutes to 10 hours.

Temperature at the pressure filtration must be in a range where the enzyme is not denatured, and is desirably about 0° to about 40° C.

In the present invention, the enzyme retained in the sponge layer in the asymmetrical membrane is cross-linked through contact with a solution of cross-linking agent, and immobilized in the porous parts of the sponge layer. The enzyme can be contacted with the solution of cross-linking agent according to any one or a combination of the following methods: a method of immersing an asymmetrical membrane retaining the enzyme in a solution of cross-linking agent, a method of spraying or coating the solution of cross-linking agent onto the asymmetrical membrane, and a method of pressure driving the solution of cross-linking agent into the asymmetrical membrane from the sponge layer side. The cross-linking agent includes, for example, dialdehydes such glutaraldehyde, dialdehyde starch, etc., isocyanate compounds such as hexamethylene diisocyanate, tolylene diisocyanate, etc., bisdiazobenzidine, N,N'-polymethylene bisiodoacetamide, N,N-ethylenebismaleimide, etc. Particularly desirable are dialdehydes such as glutaraldehyde. 10 to 1,000 parts by weight of the cross-linking agent is used per part by weight of the enzyme to be immobilized, and a concentration of the cross-linking agent in the solution is desirably 1 to 20% by weight. The cross-linking reaction time depends upon the concentration of the cross-linking agent in the solution, but usually 15 minutes to 24 hours, and the temperature for the cross-linking reaction must be in a range where the enzyme is not denatured, that is, $-10°$ C. to room temperature, preferably 0° to 5° C.

The enzyme used in the present invention includes oxidases such as glucose oxidase, amino acid oxidase, cholesterol oxidase, uricase, etc., urease, creatininase, glutaminase, penicillinase, catalase, peroxidase, invertase, mutanotase, amylase, protease such as papain, trypsin, etc., and glucose isomerase, etc. These enzymes can be immobilized singly or in a combination of two or more of them. That is, a combination of cholesterol esterase and chloresterol oxidase, a combination of glucose oxidase and catalase, and a combination of invertase and glucose oxidase or mutorotase, or the like can be improbilized together.

The present immobilized enzyme membrane can be readily produced, and has the following distinguished properties, i.e. (1) a large enzyme load, (2) a good stability against physical, chemical and biological stimuli from the outside, because the enzyme is immobilized in the sponge layer of the asymmetrical membrane, (3) a high strength, though the membrane is thin, and (4) a long life and high activity.

The present invention will be described in detail below, referring to Examples and Comparative Examples.

EXAMPLE 1

25 g of acetyl cellulose containing 39.8% by weight of acetyl groups (made by Eastman Kodak, USA), 45 g of acetone and 30 g of formamide were mixed together to prepare a casting solution. About 10 g of the casting solution was cast into a membrane having a thickness of about 75 $\mu$m on a clean, smooth glass plate by means of a Baker type applicator, and, after the solvent was evaporated for 30 seconds, the membrane together with the glass plate was immersed in cold water at 4° C. to effect gelation, whereby an asymmetrical membrane was obtained. The membrane was an reverse osmosis membrane containing a skin layer having a thickness of 1 $\mu$m and a sponge layer having a porosity of 80%. A disc having a diameter of 47 mm was cut out from the asymmetrical membrane, and subjected to the following tests as the asymmetrical membrane.

On the other hand, glucose oxidase (specific activity: 70 IU/mg (made by Boelinger Mannheim, West Germany) was dissolved in a 0.1 M phosphate buffer solution at pH 6.8 to prepare an enzyme solution (pH 6.8) having an enzyme concentration of 10 mg/ml. The resulting solution was pressure driven into the asymmetrical membrane from the sponge layer side by pressure filtration (0.5 MPa) to introduce and retain the glucose oxidase in the porous parts of the membrane.

Through the asymmetrical membrane retaining the glucose oxidase was permeated 5 ml of a 0.1 M phosphate buffer solution at pH 6.8 containing 2% by weight of glutaraldehyde under a pressure of 0.5 MPa, and then the asymmetrical membrane was immersed in 10 ml of the former solution and kept therein at 4° C. for 3 hours to effect cross-linking reaction and immobilize the glucose oxidase.

The immobilized enzyme membrane thus obtained has an activity of 0.5 IU/cm$^2$, and, after having been kept in phosphate buffer solution (0.1 M, pH 6.8) at room temperature of 30 days, the remaining activity was 80%.

Comparative Example 1

Glucose oxidase was immobilized in the same manner as in Example 1, except that a nylon porous membrane (film thickness: 130 μm, pore size: 1 μm; porosity: 80%), and the resulting membrane had an activity of 0.1 IU/cm$^2$.

Example 2

An immobilized enzyme membrane was obtained in the same manner as in Example 1, except that the asymmetrical membrane was immersed in the enzyme solution for 24 hours to introduce the enzyme therein. The resulting membrane had an activity of 0.2 IU/cm$^2$.

Example 3

An immobilized enzyme membrane was obtained in the same manner as in Example 1, except that 5 ml of glutaraldehyde was permeated through the membrane under pressure. The membrane had an activity of 0.2 IU/cm$^2$.

It is evident from the foregoing Examples 1–3 and Comparative Example 1 that the present immobilized enzyme membrane had a higher activity and thus had a higher enzyme load. It is readily comprehensible that these effects are particularly remarkable when the enzyme is pressure driven into the membrane according to pressure filtration, and a solution of cross-linking agent is permeated through the membrane under pressure.

Examples 4–11

Immobilized enzyme membranes were prepared in the same manner as in Example 1 by changing the membrane, enzyme, cross-linking agent and immobilization conditions, and the characteristics of the resulting membranes were investigated. The results are shown in the following Table, where all the enzymes used were made by Boelinger-Mannheim, West Germany.

TABLE

| Ex. No. | Asymmetrical membrane Material | Thickness (μm) | Buffer used (concentration; pH) | Enzyme solution Enzyme | Specific activity (IU/mg) | Concentration (mg/ml) |
|---|---|---|---|---|---|---|
| 4 | Aromatic polyamide | 60 | Phosphate buffer (0.1 M; 6.8) | glucose oxidase | 70 | 20 |
| 5 | Acetyl cellulose | 200 | Phosphate buffer (0.1 M; 6.8) | " | " | 10 |
| 6 | Acetyl cellulose | 75 | Phosphate buffer (0.1 M; 6.8) | " | " | 5 |
| 7 | Acetyl cellulose | 50 | Phosphate buffer (0.1 M; 6.5) | urease | 100 | 10 |
| 8 | Acetyl cellulose | 50 | Phosphate buffer (0.1 M; 6.5) | " | " | 10 |
| 9 | Acetyl cellulose | 50 | Acetic acid buffer (0.1 M; 3.5) | pepsin | 2,500 | 10 |
| 10 | Acetyl cellulose | 50 | Phosphate buffer (0.1 M; 6.0) | α-amylase | 1,800 | 10 |
| 11 | Acetyl cellulose | 50 | Phosphate buffer (0.1 M; 7.4) | cholesterol oxidase / cholesterol esterase | 25 / 20 | 3 / 3 |

| Ex. No. | Cross-linking agent | Concentration (wt. %) | Cross-linking time (hr) | Initial activity (IU/cm$^2$) | Remaining activity percent after 30 days |
|---|---|---|---|---|---|
| 4 | glutaraldehyde | 5 | 5 | 0.45 | 85 |
| 5 | " | 2 | 10 | 0.6 | 82 |
| 6 | dialdehyde starch | 5 | 10 | 0.2 | 75 |
| 7 | glutaraldehyde | 2 | 5 | 0.5 | 70 |
| 8 | hexamethylene diisocyanate | 5 | 3 | 0.3 | 76 |
| 9 | glutaraldehyde | 2 | 10 | 8 | 78 |
| 10 | " | 2 | 3 | 5 | 85 |
| 11 | " | 2 | 5 | 0.1* | 85 |

*Total activity of two enzymes

Figure 2:
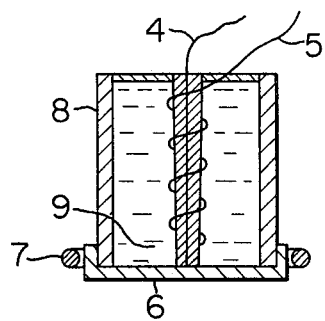
FIG. 2 is a vertical cross-sectional view of an enzyme electrode apparatus for electrochemically measuring instruments according to one embodiment of the present invention.

In FIG. 2, a vertical cross-sectional view of an enzyme electrode apparatus for electrochemically measuring instruments according to one embodiment of the present invention is shown, where a column comprised of an insulating material, at whose lower end an anode 4 is projected, is provided at a center of an insulating vessel 8 filled with an electrolyte solution 9, and a cathode 5 is wound around the column. The anode 4 and the cathode 5 are connected to a direct current source through lead wires. The upper end of the insulating vessel is sealed with an anti-corrosive plate, and the lower end is sealed with an immobilized enzyme membrane 6 according to the present invention, and is tightly fixed to the insulating vessel 8 by means of an O-ring 7.

When the immobilized enzyme membrane is made in contact with a sample solution, a substrate in the sample solution selectively reacts with the enzyme in the immobilized enzyme membrane, and consumes the oxygen in the sample solution. Thus, an equilibrium state between the electrolyte solution 9 and the sample solution is changed to change the electric current passing between the anode 4 and the cathode 5. That is, the amount of the substrate in the sample solution can be analyzed by detecting the change in the electric current. The foregoing embodiment is a case of the enzyme electrode apparatus based on a combination of the oxygen electrode and the immobilized enzyme membrane 6, and even in the cases of combinations with other kinds of electrode the present immobilized enzyme membrane 6 functions in the same manner as above, but only systems of detecting changes in electrolyte 9 are different from the above.

More specifically, a wide range of electrodes such as oxygen electrode, hydrogen peroxide electrode, ammonia electrode, ammonium electrode, carbonate ion electrode, cyan ion electrode, carbon dioxide gas electrode, iodine ion electrode, monovalent cation electrode, glass electrode, etc. can be used. A wide range of substances can be measured by the present enzyme electrode apparatus, and include, for example, glucose, urea, cholesterol, amino acid, penicillin, amygdalin, creatinine, uric acid, sucrose, lactose, etc., and analysis of other substances is possible by combinations of said various electrodes with the present immobilized enzyme membranes.

Example 12

Figure 3:
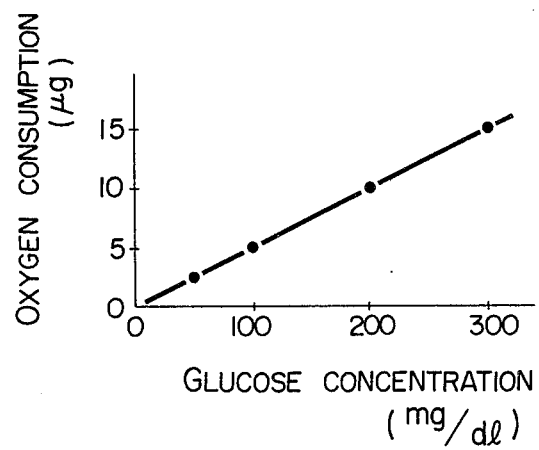
FIG. 3 is a graph showing relations between glucose concentration and oxygen consumption according to the enzyme electrode apparatus of FIG. 2.

An enzyme electrode apparatus was prepared by fixing the immobilized enzyme membrane prepared according to Example 1 to a working face of a Clark-type oxygen electrode of FIG. 2 by means of a rubber O-ring. The enzyme electrode apparatus was placed in a glucose solution at 100 mg/dl (phosphate buffer solution at pH 6.8) and an oxygen consumption in the glucose solution was measured. About 15 seconds thereafter, a steady state was attained. Then, the enzyme electrode apparatus was placed in other glucose solutions at various glucose concentrations, and the respective oxygen consumptions, 5 seconds thereafter, were measured. The results are shown in FIG. 3, where relations between the glucose concentration and the oxygen consumption by the enzyme electrode apparatus of FIG. 2 are shown. When the glucose concentration of sample solutions were set to three values, i.e. 100 mg/dl, 200 mg/dl and 300 mg/dl, the oxygen consumption was proportional to the concentration. Thus, when the present enzyme electrode apparatus is brought in contact with a sample glucose solution of unknown concentration, the glucose concentration can be rapidly analyzed with a high precision.

Comparative Example 2

To compare the present enzyme electrode apparatus of Example 12 with the prior art enzyme electrode apparatus in performance, the following test was conducted.

An immobilized enzyme membrane enclosing the same glucose oxidase as used in Example 1 by a polyacrylamide gel was prepared according to the prior art process, and the resulting immobilized enzyme membrane had a thickness of 75 $\mu$m, and the same activity as that of Example 1, and was fixed to the working face of the enzyme electrode apparatus through a polyfluorocarbon membrane having a thickness of 10 $\mu$m as a barrier membrane, that is, by laying the immobilized enzyme membrane upon the barrier membrane. When the same sample solutions of Example 12 were analyzed by means of the prior art enzyme electrode apparatus thus prepared, it took 60 seconds until a steady state was attained. That is, the response was much retarded. It shows that the retarded response is due to a poor diffusibility of the prior art immobilized enzyme membrane and the use of barrier membrane used as a barrier for preventing any electrolyte leaking and penetrating of interfaring substances.

What is claimed is:

1. An enzyme electrode apparatus for electrochemically analyzing a substance in a sample solution, which comprises a vessel for encasing an electrolyte solution therein; an anode; a cathode; an immobilized enzyme membrane containing a skin layer that functions as a barrier provided at a working face of the anode and/or cathode; and an electrolyte solution in the vessel; the immobilized enzyme membrane being provided by an asymmetrical membrane having a thickness of 30–300 $\mu$m integrally formed from a skin layer substantially incapable of permeating an enzyme therethrough, but capable of permeating a gas and a liquid therethrough, and a sponge layer having sufficient porosity for retaining a necessary amount of the enzyme and pores intercommunicated with one another throughout the sponge layer, the enzyme being immobilized in the pores of the sponge layer by cross-linking, the skin layer having a thickness of 0.1–3 $\mu$m and the sponge layer having a porosity of 50–90%; the skin layer and the sponge layer being formed from the same material.

2. An enzyme electrode apparatus according to claim 1, wherein the asymmetrical membrane is made from a material selected from the group consisting of cellulose derivatives, polyamide and polyamino acid.

3. An enzyme electrode apparatus according to claim 1, wherein the immobilized enzyme membrane is provided at a working face of the anode.

4. An enzyme electrode apparatus according to claim 1 wherein the immobilized enzyme membrane is provided at a working face of the anode and a working face of the cathode.

5. An enzyme electrode apparatus according to claim 1, wherein the immobilized enzyme membrane is provided at a working face of the cathode.

6. An enzyme electrode apparatus according to claim 1, wherein the sponge layer has pores at the surface of the sponge layer with pore sizes of about 100 to about 500 nm.

7. An enzyme electrode apparatus according to claim 1, wherein the enzyme immobilized within said pores of the sponge layer by cross-linking is selected from the group consisting of glucose oxidase, amino acid oxidase, cholesterol oxidase, uricase, urease, creatininase, glutaminase, penicillinase, catalase, peroxidase, invertase, mutanotase, amylase, protease, and glucose isomerase.

* * * * *